(12) United States Patent
Löffler et al.

(10) Patent No.: US 7,393,520 B2
(45) Date of Patent: *Jul. 1, 2008

(54) DECORATIVE COSMETIC AND DERMATOLOGICAL PRODUCTS

(75) Inventors: Matthias Löffler, Niedernhausen (DE); Roman Morschhäuser, Mainz (DE)

(73) Assignee: Clariant Produkte (Deutschland) GmbH, Sulzbach (DE)

( * ) Notice: Subject to any disclaimer, the term of this patent is extended or adjusted under 35 U.S.C. 154(b) by 821 days.

This patent is subject to a terminal disclaimer.

(21) Appl. No.: 10/433,112

(22) PCT Filed: Nov. 28, 2001

(86) PCT No.: PCT/EP01/13866

§ 371 (c)(1), (2), (4) Date: Nov. 17, 2003

(87) PCT Pub. No.: WO02/43688

PCT Pub. Date: Jun. 6, 2002

(65) Prior Publication Data

US 2004/0091444 A1 May 13, 2004

(30) Foreign Application Priority Data

Dec. 1, 2000 (DE) .................. 100 59 818

(51) Int. Cl.
*A61K 8/00* (2006.01)
*A61K 8/18* (2006.01)
*A61Q 1/00* (2006.01)
*A61Q 1/12* (2006.01)

(52) U.S. Cl. ............... 424/69; 424/78.02; 424/78.08; 424/400; 424/401

(58) Field of Classification Search ............. 424/69, 424/78.02, 78.08, 400, 401
See application file for complete search history.

(56) References Cited

U.S. PATENT DOCUMENTS

| | | | |
|---|---|---|---|
| 3,931,089 A | 1/1976 | Karl | 260/29.65 Q |
| 4,521,578 A | 6/1985 | Chen et al. | 526/288 |
| 5,104,645 A | 4/1992 | Cardin et al. | 424/70 |
| 5,368,850 A | 11/1994 | Cauwet et al. | 424/70 |
| 5,879,718 A | 3/1999 | Sebillote-Arnaud | 424/705 |
| 6,054,138 A | 4/2000 | Trebosc et al. | 424/401 |
| 6,083,491 A | 7/2000 | Mellul et al. | 424/63 |
| 6,120,780 A * | 9/2000 | Dupuis et al. | 424/401 |
| 6,403,074 B1 | 6/2002 | Blankenburg | |
| 6,419,912 B1 | 7/2002 | Lezer | 424/78.03 |
| 6,468,549 B1 | 10/2002 | Dupuis et al. | 424/401 |
| 6,524,564 B1 | 2/2003 | Kim et al. | 424/70.12 |

FOREIGN PATENT DOCUMENTS

| | | |
|---|---|---|
| CA | 2363079 | 8/2000 |
| EP | 0 356 241 | 2/1990 |
| EP | 0 504 066 | 9/1992 |
| EP | 0 815 828 | 1/1998 |
| EP | 0 815 844 | 1/1998 |
| EP | 0 815 845 | 1/1998 |
| FR | 2 791 558 | 10/2000 |
| WO | WO 99/04750 | 2/1999 |
| WO | WO 00/12053 | 3/2000 |
| WO | WO 00/12588 | 3/2000 |

OTHER PUBLICATIONS

English abstract for JP 58-099407, "Surfactant-free emulsion cosmetics—comprising water, oil component and emulsion and consisting of water-insoluble and water absorbable polymer", Sep. 25, 1993.

English Translation of PCT IPER for PCT/EP01/13866, Dated Feb. 26, 2003.

* cited by examiner

*Primary Examiner*—Michael G. Hartley
*Assistant Examiner*—Paul Dickinson
(74) *Attorney, Agent, or Firm*—Richard P. Silverman

(57) ABSTRACT

The invention provides decorative cosmetic and dermatological compositions comprising at least one copolymer obtained by free-radical copolymerization of A) acryloyld imethyltaurine and/or acryloyld imethyltaurates,
B) optionally, one or more further olefinically unsaturated, noncationic comonomers,
C) optionally, one or more olefinically unsaturated, cationic comonomers,
D) optionally, one or more silicon-containing components capable of free radical polymerization,
E) optionally, one or more fluorine-containing components,
F) optionally, one or more macromonomers,
G) optionally, the copolymerization taking place in the presence of at least one polymeric additive,
H) with the proviso that component A) is copolymerized with at least one component selected from one of the groups D) to G).

29 Claims, No Drawings

DECORATIVE COSMETIC AND DERMATOLOGICAL PRODUCTS

Decorative cosmetic products are available in a variety of forms, examples of which are powders, suspensions, dispersions, creams, and gels. Emulsions are preferred, in the form of both O/W and W/O emulsions. Emulsions are generally prepared using anionic, nonionic and/or amphoteric emulsifiers. Conventional emulsifier-containing emulsions of this kind often lead to instances of skin irritation, particularly on long-lasting and frequent application. In the case of O/W emulsions, polyquaterniums are examples of the compounds used as gelling agents for the aqueous phase. The pigment uptake capacity in the gel phase and the fineness and stability of the emulsions are unsatisfactory. Advantageous for cosmetic emulsions are water-in-oil emulsions, which possess a skin-smoothing and moisturizing activity and give the skin a good appearance. In W/O emulsions the pigments used are transferred to the oil phase by coating or other modifications. In order to achieve sufficient adhesion of the cosmetic agents to the skin, hydrophobic film formers are added, examples being alkylated vinylpyrrolidone polymers. The hydrophobic film formers, however, are resolved by the sebum which forms, thereby lowering the adhesion of the products—moreover, unwanted color shifts may occur in the pigments.

In another known mode of preparing decorative cosmetic products, hydrophilic film formers are added to the external, water phase of oil-in-water emulsions. A disadvantage here is that the colors before and after the products are applied are very different.

Surprisingly it has now been found that a new class of copolymers based on acryloyidimethyltaurine—and suitable in the capacity of a thickener, bodying agent, emulsifier, film former, adhesive, lubricant, dispersant and/or stabilizer—are outstandingly suitable for the formulation of a multiplicity of decorative cosmetic products.

The invention accordingly provides decorative cosmetic and dermatological compositions comprising at least one copolymer obtainable by free-radical copolymerization of A) acryloyldimethyltaurine and/or acryloyldimethyltaurates, B) if desired, one or more further olefinically unsaturated, noncationic, optionally crosslinking, comonomers which have at least one oxygen, nitrogen, sulfur or phosphorus atom and possess a molecular weight of less than 500 g/mol, C) if desired, one or more olefinically unsaturated, cationic comonomers which have at least one oxygen, nitrogen, sulfur or phosphorus atom and possess a molecular weight of less than 500 g/mol, D) if desired, one or more silicon-containing components capable of free-radical polymerization and having a functionality of at least one, E) if desired, one or more fluorine-containing components capable of free-radical polymerization and having a functionality of at least one, F) if desired, one or more olefinically mono- or polyunsaturated, optionally crosslinking macromonomers each possessing at least one oxygen, nitrogen, sulfur or phosphorus atom and having a number-average molecular weight of greater than or equal to 200 g/mol, the macromonomers not being a silicon-containing component D) or fluorine-containing component E), G) the copolymerization taking place if desired in the presence of at least one polymeric additive having number-average molecular weights of from 200 g/mol to $10^9$ g/mol, H) with the proviso that component A) is copolymerized with at least one component selected from one of the groups D) to G).

The copolymers of the invention preferably possess a molecular weight of from $10^3$ g/mol to $10^9$ g/mol, more preferably from $10^4$ to $10^7$ g/mol, with particular preference from $5*10^4$ to $5*10^6$ g/mol.

The acryloyidimethyltaurates can be the organic or inorganic salts of acryloyldimethyltaurine (acrylamidopropyl-2-methyl-2-sulfonic acid). Preference is given to the $Li^+$, $Na^+$, $K^+$, $Mg^{++}$, $Ca^{++}$, $Al^{+++}$ and/or $NH_4^+$ salts. Likewise preferred are the monoalkylammonium, dialkylammonium, trialkylammonium and/or tetraalkylammonium salts, in which the alkyl substituents of the amines may independently of one another be $(C_1-C_{22})$-alkyl radicals or $(C_2-C_{10})$-hydroxyalkyl radicals. Preference is also given to mono- to triethoxylated ammonium compounds with different degrees of ethoxylation. It should be noted that mixtures of two or more of the abovementioned representatives are also embraced by the invention.

The degree of neutralization of the acryloyldimethyltaurine can be between 0 and 100%, with particular preference being given to a degree of neutralization of more than 80%.

Based on the total mass of the copolymers, the amount of acryloyldimethyltaurine and/or acryloyldimethyltaurates is at least 0.1% by weight, preferably from 20 to 99.5% by weight, more preferably from 50 to 98% by weight.

As comonomers B) it is possible to use all olefinically unsaturated noncationic monomers whose reaction parameters allow copolymerization with acryloyldimethyltaurine and/or acryloyldimethyltaurates in the respective reaction media. Preferred comonomers B) are unsaturated carboxylic acids and their anhydrides and salts, and also their esters with aliphatic, olefinic, cycloaliphatic, arylaliphatic or aromatic alcohols having a carbon number of from 1 to 30.

Particularly preferred unsaturated carboxylic acids are acrylic acid, methacrylic acid, styrenesulfonic acid, maleic acid, fumaric acid, crotonic acid, itaconic acid, and senecic acid.

Preferred counterions are $Li^+$, $Na^+$, $K^+$, $Mg^{++}$, $Ca^{++}$, $Al^{+++}$, $NH_4^+$, monoalkylammonium dialkylammonium, trialkylammonium and/or tetraalkylammonium radicals, in which the alkyl substituents of the amines independently of one another can be $(C_1-C_{22})$-alkyl radicals or 3 $(C_2-C_{10})$-hydroxyalkyl radicals. It is additionally possible to employ mono- to triethoxylated ammonium compounds with a different degree of ethoxylation. The degree of neutralization of the carboxylic acids can be between 0 and 100%.

Further preferred comonomers B) are open-chain N-vinyl amides, preferably N-vinylformamide (VIFA), N-vinylmethylformamide, N-vinylmethylacetamide (VIMA) and N-vinylacetamide; cyclic N-vinyl amides (N-vinyl lactams) with a ring size of 3 to 9, preferably N-vinylpyrrolidone (NVP) and N-vinylcaprolactam; amides of acrylic and methacrylic acid, preferably acrylamide, methacrylamide, N,N-dimethylacrylamide, N,N-diethylacrylamide, and N,N-diisopropylacrylamide; alkoxylated acrylamides and methacrylamides, preferably hydroxyethyl methacrylate, hydroxymethylmethacrylamide, hydroxyethylmethacrylamide, hydroxypropylmethacrylamide, and mono [2-(methacryloyloxy)ethyl]succinate; N,N-dimethylamino methacrylate; diethylaminomethyl methacrylate; acrylamido- and methacrylamidoglycolic acid; 2- and 4-vinylpyridine; vinyl acetate; glycidyl methacrylate; styrene; acrylonitrile; vinyl chloride; stearyl acrylate; lauryl methacrylate; vinylidene chloride; and/or tetrafluoroethylene.

Likewise suitable comonomers B) are inorganic acids and their salts and esters. Preferred acids are vinylphosphonic acid, vinylsulfonic acid, allylphosphonic acid, and methallylsulfonic acid.

The weight fraction of the comonomers B), based on the total mass of the copolymers, can be from 0 to 99.8% by weight and is preferably from 0.5 to 80% by weight, more preferably from 2 to 50% by weight.

Suitable comonomers C) include all olefinically unsaturated monomers with cationic charge which are capable of forming copolymers with acryloyidimethyltaurine or its salts in the chosen reaction media. The resulting distribution of the cationic charges across the chains can be random, alternating, blocklike or gradientlike. It may be noted that the cationic comonomers C) also comprehend those which bear the cationic charge in the form of a betaine, zwitterionic or amphoteric structure. Comonomers C) for the purposes of the invention are also amino-functionalized precursors which can be converted by polymer-analogous reactions into their corresponding quaternary derivatives (e.g., reaction with dimethyl sulfate, methyl chloride), zwitterionic derivatives (e.g., reaction with hydrogen peroxide), betaine derivatives (e.g., reaction with chloroacetic acid), or amphomeric derivatives.

Particularly preferred comonomers C) are
diallyldimethylammonium chloride (DADMAC),
[2-(methacryloyloxy)ethyl]trimethylammonium chloride (MAPTAC),
[2-(acryloyloxy)ethyl]trimethylammonium chloride,
[2-methacrylamidoethyl]trimethylammonium chloride,
[2-(acrylamido)ethyl]trimethylammonium chloride,
N-methyl-2-vinylpyridinium chloride,
N-methyl-4-vinylpyridinium chloride,
dimethylaminoethyl methacrylate,
dimethylaminopropylmethacrylamide,
methacryloylethyl N-oxide and/or
methacryloylethylbetaine.

The weight fraction of the comonomers C), based on the total mass of the copolymers, can be from 0.1 to 99.8% by weight, preferably from 0.5 to 30% by weight, very preferably from 1 to 20% by weight.

Suitable polymerizable silicon-containing components D) are all compounds which are olefinically at least monounsaturated and capable of free-radical copolymerization under the reaction conditions chosen in each case. The distribution of the individual silicone-containing monomers across the polymer chains which form need not necessarily be random. The invention also embraces the formation, for example, of blocklike (including multiblock) or gradientlike structures. Combinations of two or more different silicone-containing representatives are also possible. The use of silicone-containing components having two or more polymerization-active groups leads to the construction of branched or crosslinked structures.

Preferred silicone-containing components are those of formula (I).

$$R^1\text{-}Z\text{-}[(Si(R^3R^4)\text{---}O\text{---})_w\text{---}(Si(R^5R^6)\text{---}O)_x\text{---}]\text{---}R^2 \quad (I)$$

In this formula $R^1$ represents a polymerizable function from the group of the vinylically unsaturated compounds which is suitable for the synthesis of polymeric structures by a free-radical route. $R^1$ represents preferably a vinyl, allyl, methallyl, methylvinyl, acryloyl ($CH_2$=CH—CO—), methacryloyl ($CH_2$=C[$CH_3$]—CO—), crotonyl, senecionyl, itaconyl, maleyl, fumaryl or styryl radical.

The attachment of the silicone-containing polymer chain to the reactive end group $R^1$ requires a suitable chemical bridge Z. Preferred bridges Z are —O—, [—(($C_1$-$C_{50}$)alkylene)-, —(($C_6$-$C_{30}$)arylene)-, —(($C_5$-$C_8$) cycloalkylene)-, —(($C_1$-$C_{50}$)alkenylene)-, -(polypropylene oxide)$_n$—, -(polyethylene oxide)$_o$-, -(polypropylene oxide)$_n$(polyethylene oxide)$_o$-, where n and o independently of one another denote numbers from 0 to 200 and the distribution of the EO/PO units can be random or in the form of blocks. Further suitable bridge groups Z are —(($C_1$-$C_{10}$)alkyl)(Si(OCH$_3$)$_2$)— and —(Si(OCH$_3$)$_2$)—.

The polymeric central moiety is represented by silicone-containing repeating units. Radicals $R^3$, $R^4$, $R^5$, and $R^6$ denote independently of one another —CH$_3$, —O—CH$_3$, —C$_6$H$_5$ or —O—C$_6$H$_5$.

The indices w and x represent stoichiometric coefficients which amount independently of one another to from 0 to 500, preferably 10 to 250.

The distribution of the repeating units across the chain can be not only purely random but also blocklike, alternating or gradientlike.

$R^2$ can first be an aliphatic, olefinic, cycloaliphatic, arylaliphatic or aromatic ($C_1$-$C_{50}$) hydrocarbon radical (linear or branched) or —OH, —NH$_2$, —N(CH$_3$)$_2$, —$R^7$ or stand for the structural unit [-Z-$R^1$]. The definition of the two variables Z and $R^1$ has already been explained. $R^7$ stands for further Si-containing groups. Preferred radicals $R^7$ are —O—Si(CH$_3$)$_3$, —O—Si(Ph)$_3$, —O—Si(O—Si(CH$_3$)$_3$)$_2$CH$_3$) and —O—Si(O—Si(Ph)$_3$)$_2$Ph). If $R^2$ is an element of the group [-Z-$R^1$] the monomers in question are difunctional monomers which can be used to crosslink the polymer structures which form. Formula (I) describes not only silicone-containing polymer species with vinylic functionalization and a polymer-typical distribution, but also defined compounds having discrete molecular weights.

Particularly preferred silicone-containing components are the following components with acrylic or methacrylic modification:

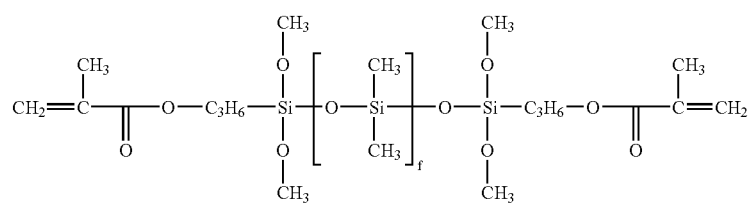

methacryloyloxypropyldimethylsilyl-endblocked polydimethylsiloxanes (f=2 to 500)

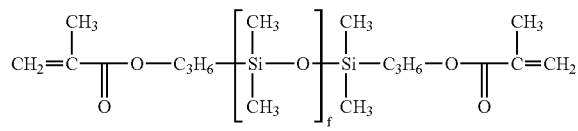

methacryloyloxypropyl-endblocked polydimethylsiloxanes (f=2 to 500)

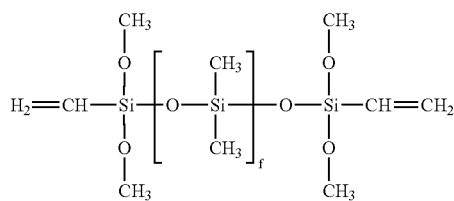

vinyldimethoxysilyl-endblocked polydimethylsiloxanes (f=2-500).

Based on the total mass of the copolymers, the amount of silicon-containing components can be up to 99.9% by weight, preferably from 0.5 to 30% by weight, more preferably from 1 to 20% by weight.

Suitable polymerizable fluorine-containing components E) include all compounds which are olefinically at least monounsaturated and which are capable of free-radical copolymerization under the reaction conditions chosen in each case. The distribution of the individual fluorine-containing monomers across the polymer chains which form need not necessarily be random. The invention also embraces the formation of blocklike (including multiblock) or gradientlike structures, for example. Combinations of two or more different fluorine-containing components E) are also possible, it being clear to the expert that monofunctional representatives lead to the formation of comb-shaped structures while di-, tri-, or polyfunctional components E) lead to structures which are at least partly crosslinked.

Preferred fluorine-containing components E) are those of formula (II).

$$R^1-Y-C_rH_{2r}C_sF_{2s}CF_3 \quad (II)$$

In this formula $R^1$ represents a polymerizable function from the group of the vinylically unsaturated compounds which is suitable for the construction of polymeric structures by a free-radical route. $R^1$ is preferably a vinyl, allyl, methallyl, methylvinyl, acryloyl ($CH_2$=CH—CO—), methacryloyl ($CH_2$=C[$CH_3$]—CO—), crotonyl, senecionyl, itaconyl, maleyl, fumaryl or styryl radical, more preferably an acryloyl or methacryloyl radical.

The attachment of the fluorine-containing group to the reactive end group $R^1$ requires a suitable chemical bridge Y. Preferred bridges Y are —O—, —C(O)—, —C(O)—O—, —S—, —O—C H$_2$—CH (O—)—CH$_2$OH, —O—CH$_2$—CH(OH) —CH$_2$—O—, —O—SO$_2$—O—, —O—S(O)—O—, —PH—, —P(CH$_3$)—, —PO$_3$—, —NH—, —N(CH$_3$)—, —O—(C$_1$-C$_{50}$)alkyl-O—, —O-phenyl-O—, —O-benzyl-O—, —O—(C$_5$-C$_8$)cycloalkyl-O—, —O—(C$_1$-C$_{50}$)alkenyl-O—, —O—(CH(CH$_3$)—CH$_2$—O)$_n$—, —O—(CH$_2$—CH$_2$—O)$_n$—, and —O—([CH—CH$_2$—O]$_n$—[CH$_2$—CH$_2$—O]$_m$)$_o$—, where n, m, and o independently of one another denote numbers from 0 to 200 and the distribution of the EO and PO units can be random or in the form of blocks. r and s are stoichiometric coefficients which independently of one another denote numbers from 0 to 200.

Preferred fluorine-containing components E) of formula (II) are
perfluorohexylethanol methacrylate,
perfluorohexoylpropanol methacrylate,
perfluorooctylethanol methacrylate,
perfluorooctylpropanol methacrylate,
perfluorohexylethanolyl polyglycol ether methacrylate,
perfluorohexoylpropanolyl poly[ethylglycol-co-propylene glycol ether]acrylate,
perfluorooctylethanolyl poly[ethylglycol-block-co-propylene glycol ether]methacrylate,
perfluorooctylpropanolyl polypropylene glycol ether methacrylate.

Based on the total mass of the copolymers the amount of suitable fluorine-containing components can be up to 99.9% by weight, preferably from 0.5 to 30% by weight, more preferably from 1 to 20% by weight.

The macromonomers F) are at least singly olefinically functionalized polymers having one or more discrete repeating units and a number-average molecular weight of greater than or equal to 200 g/mol. In the copolymerization it is also possible to use mixtures of chemically different macromonomers F). The macromonomers are polymeric structures composed of one or more repeating units and have a molecular weight distribution characteristic of polymers. Preferred macromonomers F) are compounds of formula (III).

$$R^1-Y-[(A)_v-(B)_w-(C)_x-(D)_z]-R^2 \quad (III)$$

$R^1$ represents a polymerizable function from the group of the vinylically unsaturated compounds which are suitable for constructing polymeric structures by a free-radical route. Preferably $R^1$ is a vinyl, allyl, methallyl, methylvinyl, acryloyl ($CH_2$=CH—CO—), methacryloyl ($CH_2$=[$CH_3$]—CO—), crotonyl, senecionyl, itaconyl, maleyl, fumaryl or styryl radical.

Attachment of the polymer chain to the reactive end group requires a suitable bridging group Y. Preferred bridges Y are —O—, —C(O)—, —C(O)—O—, —S—, —O—CH$_2$—CH (O—)—CH$_2$OH, —O—CH$_2$—CH(OH)—CH$_2$O—, —O—SO$_2$—O—, —O—SO$_2$—O—, —O—SO—O—, —PH—, —P(CH$_3$)—, —PO$_3$—, —NH—, and —N(CH$_3$)—, more preferably —O—.

The polymeric central moiety of the macromonomer is represented by the discrete repeating units A, B, C, and D. Preferably the repeating units A, B, C, and D are derived from: acrylamide, methacrylamide, ethylene oxide, propylene oxide, AMPS, acrylic acid, methacrylic acid, methyl methacrylate, acrylonitrile, maleic acid, vinyl acetate, styrene, 1,3-butadiene, isoprene, isobutene, diethylacrylamide, and diisopropylacrylamide.

The indices v, w, x, and z in formula (III) represent the stoichiometric coefficients relating to the repeating units A, B, C, and D. v, w, x, and z amount independently of one another to from 0 to 500, preferably 1 to 30, it being necessary for the sum of the four coefficients on average to be $\geq 1$.

The distribution of the repeating units over the macromonomer chain can be random, blocklike, alternating or gradientlike.

$R^2$ denotes a linear or branched aliphatic, olefinic, cycloaliphatic, arylaliphatic or aromatic (C$_1$-C$_{50}$) hydrocarbon radical, OH, —NH$_2$, —N(CH$_3$)$_2$ or is the structural unit [—Y—R$^1$].

In the case of $R^2$ being [—Y—$R^1$] the macromonomers in question are difunctional and suitable for crosslinking the copolymers.

Particularly preferred macromonomers F) are acrylically or methacrylically monofunctionalized alkyl ethoxylates of formula (IV).

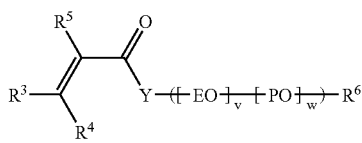

$R_3$, $R_4$, $R_5$, and $R_6$ are independently of one another hydrogen or n-aliphatic, isoaliphatic, olefinic, cycloaliphatic, arylaliphatic or aromatic ($C_1$-$C_{30}$) hydrocarbon radicals.

Preferably $R_3$ and $R_4$ are H or —$CH_3$, more preferably H; $R_5$ is H or —$CH_3$; and $R_6$ is an n-aliphatic, iso-aliphatic, olefinic, cycloaliphatic, arylaliphatic or aromatic ($C_1$-$C_{30}$) hydrocarbon radical.

v and w are in turn the stoichiometric coefficients relating to the ethylene oxide units (EO) and propylene oxide units (PO). v and w amount independently of one another to from 0 to 500, preferably 1 to 30, it being necessary for the sum of v and w to be on average $\geq 1$. The distribution of the EO and PO units over the macromonomer chain can be random, blocklike, alternating or gradientlike. Y stands for the above-mentioned bridges.

Further particularly preferred macromonomers F) have the following structure in accordance with formula (IV):

| Name | $R^3$ | $R^4$ | $R^5$ | $R^6$ | v | w |
|---|---|---|---|---|---|---|
| ®LA-030-methacrylate | H | H | —$CH_3$ | -lauryl | 3 | 0 |
| ®LA-070-methacrylate | H | H | —$CH_3$ | -lauryl | 7 | 0 |
| ®LA-200-methacrylate | H | H | —$CH_3$ | -lauryl | 20 | 0 |
| ®LA-250-methacrylate | H | H | —$CH_3$ | -lauryl | 25 | 0 |
| ®T-080-methacrylate | H | H | —$CH_3$ | -talc | 8 | 0 |
| ®T-080-acrylate | H | H | H | -talc | 8 | 0 |
| ®T-250-methacrylate | H | H | —$CH_3$ | -talc | 25 | 0 |
| ®T-250-crotonate | —$CH_3$ | H | —$CH_3$ | -talc | 25 | 0 |
| ®OC-030-methacrylate | H | H | —$CH_3$ | -octyl | 3 | 0 |
| ®OC-105-methacrylate | H | H | —$CH_3$ | -octyl | 10 | 5 |
| ®Behenyl-010-methylaryl | H | H | H | -behenyl | 10 | 0 |
| ®Behenyl-020-methylaryl | H | H | H | -behenyl | 20 | 0 |
| ®Behenyl-010-senecionyl | —$CH_3$ | —$CH_3$ | H | -behenyl | 10 | 0 |
| ®PEG-440-diacrylate | H | H | H | -acryloyl | 10 | 0 |
| ®B-11-50-methacrylate | H | H | —$CH_3$ | -butyl | 17 | 13 |
| ®MPEG-750-methacrylate | H | H | —$CH_3$ | -methyl | 18 | 0 |
| ®P-010-acrylate | H | H | H | -phenyl | 10 | 0 |
| ®O-050-acrylate | H | H | H | -oleyl | 5 | 0 |

Further particularly suitable macromonomers F) are esters of (meth)acrylic acid with ($C_{10}$-$C_{18}$) fatty alcohol polyglycol ethers having 8 EO units (Genapol® C-080)

$C_{11}$ oxo alcohol polyglycol ethers having 8 EO units (Genapol® UD-080)

($C_{12}$-$C_{14}$) fatty alcohol polyglycol ethers having 7 EO units (Genapol® LA-070)

($C_{12}$-$C_{14}$) fatty alcohol polyglycol ethers having 11 EO units (Genapol® LA-110)

($C_{16}$-$C_{18}$) fatty alcohol polyglycol ethers having 8 EO units (Genapol® T-080)

($C_{16}$-$C_{18}$) fatty alcohol polyglycol ethers having 15 EO units (Genapol® T-150)

($C_{16}$-$C_{18}$) fatty alcohol polyglycol ethers having 11 EO units (Genapol® T-110)

($C_{16}$-$C_{18}$) fatty alcohol polyglycol ethers having 20 EO units (Genapol® T-200)

($C_{16}$-$C_{18}$) fatty alcohol polyglycol ethers having 25 EO units (Genapol® T-250)

($C_{18}$-$C_{22}$) fatty alcohol polyglycol ethers having 25 EO units and/or iso-($C_{16}$-$C_{18}$) fatty alcohol polyglycol ethers having 25 EO units.

The Genapol® grades are products of Clariant GmbH.

The molecular weight of the macromonomers F) is preferably from 200 g/mol to $10^6$ g/mol, more preferably from 150 to 104 g/mol, and very preferably from 200 to 5000 g/mol.

Based on the total mass of the copolymers it is possible to use suitable macromonomers up to 99.9% by weight. The ranges used are preferably from 0.5 to 30% by weight and from 70 to 99.5% by weight. Particularly preferred are fractions of from 1 to 20% by weight and from 75 to 95% by weight.

Preferred copolymers are those obtainable by copolymerizing at least components A), C) and D).

Further preferred copolymers are those obtainable by copolymerizing at least components A), C) and E).

Further preferred copolymers are those obtainable by copolymerizing at least components A), C) and F).

Further preferred copolymers are those obtainable by copolymerizing at least components A), D) and F).

Further preferred copolymers are those obtainable by copolymerizing at least components A) and F).

Further preferred copolymers are those obtainable by copolymerizing at least components A) and D).

Further preferred copolymers are those obtainable by copolymerizing at least components A) and E).

In one preferred embodiment the copolymerization is conducted in the presence of at least one polymeric additive G), the additive G) being added wholly or partly in solution to the polymerization medium before the actual copolymerization. The use of two or more additives G) is likewise in accordance with the invention.

Crosslinked additives G) may likewise be used.

The additives G) or mixtures thereof must only be wholly or partly soluble in the chosen polymerization medium. During the actual polymerization step the additive G) has a number of functions. On the one hand it prevents the formation of overcrosslinked polymer fractions in the copolymer which forms in the actual polymerization step, and on the other hand the additive G) is statistically attacked by active free radicals in accordance with the very well-known mechanism of graft copolymerization. Depending on the particular additive G), this results in greater or lesser fractions of the additive being incorporated into the copolymers. Moreover, suitable additives G) possess the property of altering the solution parameters of the copolymers which form during the free-radical polymerization reaction in such a way that the average molecular weights are shifted to higher values. As compared with analogous copolymers prepared without the addition of the additives G), those prepared with the addition of additives G) advantageously exhibit a significantly higher viscosity in aqueous solution.

Preferred additives G) are homopolymers and copolymers which are soluble in water and/or alcohols, preferably in t-butanol. The term "copolymers" also comprehends those having more than two different monomer types.

Particularly preferred additives G) are homopolymers and copolymers of N-vinylformamide, N-vinylacetamide, N-vinylpyrrolidone, ethylene oxide, propylene oxide, acryloyldimethyltaurine, N-vinylcaprolactam, N-vinylmethylacetamide, acrylamide, acrylic acid, methacrylic acid, N-vinylmorpholide, hydroxyethyl methacrylate, diallyldimethylammonium chloride (DADMAC) and/or [2-(methacryloyloxy)ethyl]trimethylammonium chloride (MAPTAC); polyalkylene glycols and/or alkylpolyglycols.

Particularly preferred additives G) are polyvinylpyrrolidones (e.g., Luviskol K15®, K20® and K30® from BASF), poly(N-vinylformamides), poly(N-vinylcaprolactams), and copolymers of N-vinylpyrrolidone, N-vinylformamide and/or acrylic acid, which may also have been partly or fully hydrolyzed.

The molecular weight of the additives G) is preferably from $10^2$ to $10^7$ g/mol, more preferably from $0.5*10^4$ to $10^6$ g/mol.

The amount in which the polymeric additive G) is used, based on the total mass of the monomers to be polymerized during the copolymerization, is preferably from 0.1 to 90% by weight, more preferably from 1 to 20% by weight, and with particular preference from 1.5 to 10% by weight.

In another preferred embodiment the copolymers of the invention are crosslinked, i.e., they contain comonomers having at least two polymerizable vinyl groups. Preferred crosslinkers are methylenebisacrylamide; methylenebismethacrylamide; esters of unsaturated monocarboxylic and polycarboxylic acids with polyols, preferably diacrylates and triacrylates, dimethacrylates and trimethacrylates, more preferably butanediol and ethylene glycol diacrylate and methacrylate, trimethylolpropane triacrylate (TMPTA) and trimethylolpropane trimethacrylate (TMPTMA); allyl compounds, preferably allyl (meth)acrylate, triallyl cyanurate, diallyl maleate, polyallyl esters, tetraallyloxyethane, triallylamine, tetraallylethylenediamine; allyl esters of phosphoric acid; and/or vinylphosphonic acid derivatives. A particularly preferred crosslinker is trimethylolpropane triacrylate (TMPTA). The weight fraction of crosslinking comonomers, based on the total mass of the copolymers, is preferably up to 20% by weight, more preferably from 0.05 to 10% by weight, and very preferably from 0.1 to 7% by weight.

The polymerization medium used may comprise all organic or inorganic solvents which have a very substantially inert behavior with respect to free-radical polymerization reactions and which advantageously allow the formation of medium or high molecular weights. Those used preferably include water; lower alcohols; preferably methanol, ethanol, propanols, iso-, sec- and t-butanol, very preferably t-butanol; hydrocarbons having 1 to 30 carbon atoms, and mixtures of the aforementioned compounds.

The polymerization reaction takes place preferably in the temperature range between 0 and 150° C., more preferably between 10 and 100° C., either at atmospheric pressure or under elevated or reduced pressure. If desired the polymerization may also be performed under an inert gas atmosphere, preferably under nitrogen.

In order to initiate the polymerization it is possible to use high-energy electromagnetic rays, mechanical energy, or the customary chemical polymerization initiators, such as organic peroxides, e.g., benzoyl peroxide, tert-butyl hydroperoxide, methyl ethyl ketone peroxide, cumene hydroperoxide, dilauroyl peroxide or azo initiators, such as azodiisobutyronitrile (AIBN), for example.

Likewise suitable are inorganic peroxy compounds, such as $(NH_4)_2S_2O_8$, $K_2S_2O_8$ or $H_2O_2$, for example, where appropriate in combination with reducing agents (e.g., sodium hydrogensulfite, ascorbic acid, iron(II) sulfate, etc.) or redox systems comprising as reducing component an aliphatic or aromatic sulfonic acid (e.g., benzenesulfonic acid, toluenesulfonic acid, etc.).

Serving as the polymerization medium may be any solvents which are very substantially inert in respect of free-radical polymerization reactions and which allow the development of high molecular weights. Use is preferably made of water and lower, tertiary alcohols or hydrocarbons having 3 to 30 carbon atoms. In one particularly preferred embodiment t-butanol is used as the reaction medium. Mixtures of two or more representatives of the potential solvents described are of course likewise in accordance with the invention. This also includes emulsions of mutually immiscible solvents (e.g., water/hydrocarbons). In principle, all kinds of reaction regime leading to the polymer structures of the invention are suitable (solution polymerization, emulsion methods, precipitation methods, high-pressure methods, suspension methods, bulk polymerization, gel polymerization, and so on).

Preferred suitability is possessed by precipitation polymerization, particularly preferred suitability by precipitation polymerization in tert-butanol.

The following list shows 67 copolymers with particular suitability for formulating the compositions of the invention. The different copolymers 1 to 67 are obtainable in accordance with the following preparation processes 1, 2, 3, and 4.

Process 1:

These polymers can be prepared by the precipitation method in tert-butanol. The monomers were introduced in t-butanol, the reaction mixture was rendered inert, and then, after initial heating to 60° C., the reaction was initiated by addition of the corresponding t-butanol-soluble initiator (preferably dilauroyl peroxide). After the end of reaction (2 hours) the polymers were isolated by removal of the solvent under suction and by subsequent vacuum drying.

Process 2:

These polymers are preparable by the gel polymerization method in water. The monomers are dissolved in water, the reaction mixture is rendered inert, and then, after initial heating to 65° C., the reaction is initiated by addition of suitable initiators or initiator systems (preferably $Na_2S_2O_8$). The polymer gels are subsequently comminuted and the polymers are isolated after drying.

Process 3:

These polymers are preparable by the emulsion method in water. The monomers are emulsified in a mixture of water/organ. solvent (preferably cyclohexane) using an emulsifier, the reaction mixture is rendered inert by means of $N_2$, and then, after initial heating to 80° C., the reaction is initiated by addition of suitable initiators or initiator systems (preferably $Na_2S_2O_8$). The polymer emulsions are subsequently evaporated down (with cyclohexane acting as an azeotrope former for water) and the polymers are thereby isolated.

Process 4:

These polymers are preparable by the solution method in organic solvents (preferably toluene, also, for example, tertiary alcohols) The monomers are introduced in the solvent, the reaction mixture is rendered inert, and then, after initial heating to 70° C., the reaction is initiated by addition of suitable initiators or initiator systems (preferably dilauroyl peroxide). The polymers are isolated by evaporating off the solvent and by subsequent vacuum drying.

| No. | Composition | Preparation process |
|---|---|---|
| | Polymers having hydrophobic side chains, uncrosslinked | |
| 1 | 95 g AMPS 5 g Genapol T-080 | 1 |
| 2 | 90 g AMPS 10 g Genapol T-080 | 1 |
| 3 | 85 g AMPS 15 g Genapol T-080 | 1 |
| 4 | 80 g AMPS 20 g Genapol T-080 | 1 |
| 5 | 70 g AMPS 30 g Genapol T-080 | 1 |
| 6 | 50 g AMPS 50 g Genapol T-080 | 3 |
| 7 | 40 g AMPS 60 g Genapol T-080 | 3 |
| 8 | 30 g AMPS 70 g Genapol T-080 | 3 |
| 9 | 20 g AMPS 80 g Genapol T-080 | 3 |
| 10 | 60 g AMPS 60 g BB10 | 4 |
| 11 | 80 g AMPS 20 g BB10 | 4 |
| 12 | 90 g AMPS 10 g BB10 | 3 |
| 13 | 80 g AMPS 20 g BB10 | 1 |
| 14 | 80 g AMPS 20 g Genapol LA040 | 1 |
| | Polymers having hydrophobic side chains, crosslinked | |
| 15 | 80 g AMPS 20 g Genapol LA040 0.6 g AMA | 1 |
| 16 | 80 g AMPS 20 g Genapol LA040 0.8 g AMA | 1 |
| 17 | 80 g AMPS 20 g Genapol LA040 1.0 g AMA | 1 |
| 18 | 628.73 g AMPS 120.45 g Genapol T-250 6.5 g TMPTA | 2 |
| 19 | 60 g AMPS 40 g BB10 1.9 g TMPTA | 4 |
| 20 | 80 g AMPS 20 g BB10 1.4 g TMPTA | 4 |
| 21 | 90 g AMPS 10 g BB10 1.9 g TMPTA | 4 |
| 22 | 80 g AMPS 20 g BB10 1.9 g TMPTA | 4 |
| 23 | 60 g AMPS 40 g BB10 1.4 g TMPTA | 4 |
| | Polymers having hydrophobic side chains, crosslinked, grafted | |
| 24 | 95 g AMPS 5 g BB10, 1.9 g TMPTA, 1 g Poly-NVP | 1 |
| 25 | 90 g AMPS 10 g BB10, 1.9 g TMPTA, 1 g Poly-NVP | 1 |
| 26 | 85 g AMPS 15 g BB10, 1.9 g TMPTA, 1 g Poly-NVP | 1 |
| 27 | 90 g AMPS 10 g BB10, 1.9 g TMPTA, 1 g Poly-NVP | 1 |
| | Polymers having silicon-containing groups, uncrosslinked | |
| 28 | 80 g AMPS, 20 g Silvet 867 | 1 |
| 29 | 80 g AMPS, 50 g Silvet 867 | 4 |
| | Polymers having silicon-containing groups, crosslinked | |
| 30 | 80 g AMPS, 20 g Silvet 867, 0.5 g MBA | 4 |
| 31 | 80 g AMPS, 20 g Silvet 867, 1.0 g MBA | 1 |
| 32 | 60 g AMPS, 40 g Y-12867, 0.95 g AMA | 1 |
| 33 | 80 g AMPS, 20 g Y-12867, 0.95 g AMA | 1 |
| 34 | 90 g AMPS, 10 g Y-12867, 0.95 g AMA | 1 |
| 35 | 60 g AMPS, 40 g Silvet 7280, 0.95 g AMA | 1 |
| 36 | 80 g AMPS, 20 g Silvet 7280, 0.95 g AMA | 1 |
| 37 | 90 g AMPS, 10 g Silvet 7280, 0.95 g AMA | 1 |
| 38 | 60 g AMPS, 40 g Silvet 7608, 0.95 g AMA | 1 |
| 39 | 80 g AMPS, 20 g Silvet 7608, 0.95 g AMA | 1 |
| 40 | 90 g AMPS, 10 g Silvet 7608, 0.95 g AMA | 1 |
| | Polymers having hydrophobic side chains and cationic groups, uncrosslinked | |
| 41 | 87.5 g AMPS, 7.5 g Genapol T-110, 5 g DADMAC | 2 |
| 42 | 40 g AMPS, 10 g Genapol T110, 45 g methacrylamide | 2 |
| 43 | 55 g AMPS, 40 g Genapol LA040, 5 g Quat | 1 |
| 44 | 75 g AMPS, 10 g BB10, 6.7 g Quat | 1 |
| | Polymers having hydrophobic side chains and cationic groups, crosslinked | |
| 45 | 60 g AMPS, 20 g Genapol T-80, 10 g Quat, 10 g HEMA | 1 |
| 46 | 75 g AMPS, 20 g Genapol T-250, 5 g Quat, 1.4 g TMPTA | 1 |
| 47 | 75 g AMPS, 20 g Genapol T-250, 10 g Quat, 1.4 g TMPTA | 1 |
| 48 | 75 g AMPS, 20 g Genapol T-250, 20 g Quat, 1.4 g TMPTA | 1 |
| | Polymers having fluorine-containing groups | |
| 49 | 94 g AMPS, 2.02 g Fluowet AC 600 | 1 |
| 50 | 80 g AMPS, 20 g perfluorooctylpolyethylene glycol methacrylate, 1 g Span 80 | 3 |
| | Polymers having fluorine-containing groups, grafted | |
| 51 | 80 g AMPS, 10 g Fluowet AC 600, 5 g Poly-NVP | 1 |
| 52 | 70 g AMPS, 8 g perfluorooctylethyloxyglyceryl methacrylate, 5 g Poly-NVP | 4 |
| | Polyfunctional polymers | |
| 53 | 80 g AMPS, 10 g Genapol LA070, 10 g Silvet 7608, 1.8 g TMPTA | 1 |
| 54 | 70 g AMPS, 5 g N-vinylpyrrolidone, 15 g Genapol T-250 methacrylate, 10 g Quat, 10 g Poly-NVP | 4 |
| 55 | 80 g AMPS, 5 g N-vinylformamide, 5 g Genapol O-150-methacrylate, 10 g DADMAC, 1.8 g TMPTA, 8 g poly-N-vinylformamide | 2 |
| 56 | 70 g AMPS, 5 g N-vinylpyrrolidone, 15 g Genapol T-250-methacrylate, 10 g Quat, 10 g Poly-NVP | 1 |
| 57 | 60 g AMPS, 10 g Genapol-BE-020-methacrylate, 10 g Genapol T-250-acrylate, 20 g Quat, 1 g Span 80 | 1 |
| 58 | 60 g AMPS, 20 g MPEG-750-methacrylate, 10 g methacryloyloxypropyldimethicone, 10 g perfluorooctylpolyethylene glycol methacrylate, 10 g poly[N-vinylcaprolactone-co-acrylic acid] (10/90) | 1 |
| 59 | 80 g AMPS, 5 g N-vinylformamide, 5 g Genapol O-150-methacrylate, 10 g DADMAC, 1.8 g TMPTA | 1 |
| 60 | 70 g AMPS, 10 g Genapol T-250-acrylate, 5 g N-methyl-4-vinylpyridinium chloride, 2.5 g Silvet Y-12867, 2.5 g perfluorohexylpolyethylene glycol methacrylate, 10 g polyethylene glycol dimethacrylate, 4 g poly[N-vinylcaprolactam] | 1 |
| 61 | 10 g AMPS, 20 g acrylamide, 30 g N-2-vinylpyrrolidone, 20 g Silvet 7608, 10 g methacryloyloxypropyldimethicone, 10 g Fluowet AC 812 | 3 |
| 62 | 60 g AMPS, 10 g DADMAC, 10 g Quat, 10 g Genapol-LA-250-crotonate, 10 g methacryloyloxypropyldimethicone, 7 g poly[acrylic acid-co-N-vinylformamide] | 1 |
| 63 | 50 g AMPS, 45 g Silvet 7608, 1.8 g TMPTA, 8 g poly[N-vinylformamide] | 1 |
| 64 | 20 g AMPS, 10 g Genapol T 110, 35 g MAA, 30 g HEMA, 5 g DADMAC | 4 |
| 65 | 20 g AMPS, 80 g BB10, 1.4 g TMPTA | 1 |
| 66 | 75 g AMPS, 20 g BB10, 6.7 g Quat, 1.4 g TMPTA | 1 |
| 67 | 35 g AMPS, 60 g acrylamide, 2 g VIFA, 2.5 g vinylphosphonic acid, 2 mol % Fluowet EA-600 | 4 |

-continued

| Chemical designation of the reactants: | |
|---|---|
| AMPS | acryloyldimethyltaurate, either Na or NH4 salt |
| Genapol ® T-080 | $C_{16}$-$C_{18}$ fatty alcohol polyglycol ether having 8 EO units |
| Genapol ® T-110 | $C_{12}$-$C_{14}$ fatty alcohol polyglycol ether having 11 EO units |
| Genapol ® T-250 | $C_{16}$-$C_{18}$ fatty alcohol polyglycol ether having 25 EO units |
| Genapol ® LA-040 | $C_{12}$-$C_{14}$ fatty alcohol polyglycol ether having 4 EO units |
| Genapol ® LA-070 | $C_{12}$-$C_{14}$ fatty alcohol polyglycol ether having 7 EO units |
| Genapol ® O-150 methacrylate | $C_{16}$-$C_{18}$ fatty alcohol polyglycol ether methacrylate having 15 EO units, |
| Genapol ® LA-250 crotonate | $C_{12}$-$C_{14}$ fatty alcohol polyglycol ether crotonate having 25 EO units |
| Genapol ® T-250 methacrylate | $C_{16}$-$C_{18}$ fatty alcohol polyglycol ether methacrylate having 25 EO units |
| Genapol ® T-250 acrylate | $C_{16}$-$C_{18}$ fatty alcohol polyglycol ether acrylate having 25 EO units |
| BB10 ® | polyoxyethylene(10)behenyl ether |
| TMPTA | trimethylolpropanetriacrylate |
| Poly-NVP | poly-N-vinylpyrrolidone |
| Silvet ® 867 | siloxane-polyalkylene oxide copolymer |
| MBA | methylenebisacrylamide |
| AMA | allyl methacrylate |
| ®Y-12867 | siloxane-polyalkylene oxide copolymer |
| Silvet ® 7608 | polyalkylene oxide-modified heptamethyltrisiloxane |
| Silvet ® 7280 | polyalkylene oxide-modified heptamethyltrisiloxane |
| DADMAC | diallyldimethylammonium chloride |
| HEMA | 2-hydroxyethyl methacrylate |
| Quat | 2-(methacryloyloxy)ethyltrimethylammonium chloride |
| Fluowet ® AC 600 | perfluoroalkylethyl acrylate |
| Span ® 80 | sorbitan ester |

In one preferred embodiment the copolymers are water-soluble or water-swellable. The described grafting of the copolymers with other polymers, which can be carried out optionally, leads to products having a particular polymer morphology and giving rise to optically clear gels in aqueous systems. A potential disadvantage of the copolymers without grafting is a more or less strong opalescence in aqueous solution. The basis for this opalescence is hitherto unavoidable, overcrosslinked polymer fractions which arise in the course of the synthesis and are inadequately swollen in water. This produces light-scattering particles whose size is well above the wavelength of visible light and which are therefore the cause of the opalescence. The described grafting process, which can be carried out optionally, substantially reduces or entirely prevents the formation of overcrosslinked polymer fractions in relation to conventional techniques.

The described incorporation both of cationic charges and of silicon, fluorine or phosphorus atoms into the copolymers, which can be carried out optionally, leads to products which in cosmetic formulations possess particular sensorial and rheological properties. An improvement in the sensorial and rheological properties is desired in particular in the context of use as leave-on products, especially in the case of emulsions.

In both crosslinked and uncrosslinked form the copolymers exhibit advantageous properties. While crosslinked systems, for example, have exhibited outstanding profiles of properties in respect of emulsifying and dispersing capacity and emulsion stabilization, it has been possible in particular with the aid of the quaternized, fluorine-containing and silicon-containing versions to achieve a good sensorial, smoothing effect of the compositions. A particular advantage is that the copolymers effectively absorb excess sebum at the same time as the compositions exhibit a lasting adhesion.

The copolymers can be used for decorative cosmetic and dermatological compositions on an aqueous or aqueous-alcoholic basis, in oil-in-water and water-in-oil emulsions and suspensions, microemulsions, and also as lubricants and adhesives in lacquers, powders, and pastes. Mixtures of the copolymers can also be used in these contexts.

The compositions of the invention contain preferably from 0.01 to 10% by weight, more preferably from 0.1 to 5% by weight, very preferably from 0.5 to 3% by weight, of copolymers.

As further auxiliaries and additives the compositions of the invention may comprise pigments and other pulverulent substances, oily substances, emulsifiers and coemulsifiers, cationic polymers, film formers, antioxidants, light stabilizers, UV light protection filters, deodorizers, antimicrobial agents, superfatting agents, moisturizing agents, stabilizers, active biogenic substances, glycerol, preservatives, pearlizing agents, fragrances, solvents, opacifiers, further thickeners and dispersants, and also protein derivatives such as gelatin, collagen hydrolysates, natural or synthetic-based polypeptides, egg yolk, lecithin, lanolin and lanolin derivatives, fatty alcohols, silicones, refresher agents, for example methyl acetate, substances with a keratolytic and keratoplastic action, enzymes and carrier substances.

Suitable pigments include metal oxides, examples being iron oxides, mica-iron oxide, titanium oxide, mica-titanium oxide, ultramarine blue, chromium oxides, and also pigments modified with cationic coating shells, as described in WO 00/12053 and EP 504 066. It is also possible to employ $SiO_2$, silica, ZnO, kaolin, $SiO_2$-modified kaolin, polytetrafluoroethylene, nylon, talc, mica, polymethyl methacrylate, polyethylene, natural organic compounds such as capsulated or unencapsulated cereal starch, and mixtures thereof.

An oily substance is any fatty substance which is liquid at room temperature (25° C.).

The fatty phase may therefore comprise one or more oils selected preferably from the following oils:

silicone oils, volatile or nonvolatile, linear, branched or cyclic, optionally with organic modification; phenylsilicones; silicone resins and silicone gums; mineral oils such as paraffin oil or vaseline oil; oils of animal origin such as perhydrosqualene, lanolin; oils of plant origin such as liquid triglycerides, e.g., sunflower oil, corn oil, soybean oil, rice oil, jojoba oil, babusscu oil, pumpkin oil, grapeseed oil, sesame oil, walnut oil, apricot oil, macadamia oil, avocado oil, sweet almond oil, lady's-smock oil, castor oil, triglycerides of caprylic/capric acids, olive oil, peanut oil, rapeseed oil, and coconut oil;

synthetic oils such as purcellin oil, isoparaffins, linear and/or branched fatty alcohols and fatty acid esters, preferably guerbet alcohols having 6 to 18, preferably 8 to 10, carbon atoms; esters of linear $C_6$-$C_{13}$ fatty acids with linear $C_6$-$C_{20}$ fatty alcohols; esters of branched $C_6$-$C_{13}$ carboxylic acids with linear $C_6$-$C_{20}$ fatty alcohols, esters of linear $C_6$-$C_{18}$ fatty acids with branched alcohols, especially 2-ethylhexanol; esters of linear and/or branched fatty acids with polyhydric alcohols (such as dimerdiol or trimerdiol, for example) and/or guerbet alcohols; triglycerides based on $C_6$-$C_{10}$ fatty acids;

esters such as dioctyl adipate, diisopropyl dimer dilinoleate; propylene glycols/dicaprylate or waxes such as beeswax, paraffin wax or microwaxes, alone or in combination with hydrophilic waxes, such as cetylstearyl alcohol, for example; fluorinated and perfluorinated oils; fluorinated silicone oils; mixtures of the aforementioned compounds.

Suitable nonionogenic coemulsifiers include adducts of from 0 to 30 mol of ethylene oxide and/or from 0 to 5 mol of propylene oxide with linear fatty alcohols having 8 to 22 carbon atoms, with fatty acids having 12 to 22 carbon atoms, with alkylphenols having 8 to 15 carbon atoms in the alkyl group, and with sorbitan or sorbitol esters; $C_{12}$-$C_{18}$ fatty acid monoesters and diesters of adducts of from 0 to 30 mol of ethylene oxide with glycerol; glycerol monoesters and diesters and sorbitan monoesters and diesters of saturated and unsaturated fatty acids having 6 to 22 carbon atoms and, where appropriate, their ethylene oxide adducts; adducts of from 15 to 60 mol of ethylene oxide with castor oil and/or hydrogenated castor oil; polyol esters and especially polyglycerol esters, such as polyglyceryl polyricinoleate and polyglyceryl poly-12-phydroxystearate, for example. Likewise suitable are mixtures of compounds from one or more of these classes of substance.

Examples of suitable ionogenic coemulsifiers include anionic emulsifiers, such as mono-, di- or tri-phosphoric esters, but also cationic emulsifiers such as mono-, di-, and tri-alkyl quats and their polymeric derivatives.

Available cationic polymers are those known under the INCI designation "Polyquaternium", especially Polyquaternium-31, Polyquaternium-16, Polyquaternium-24, Polyquaternium-7, Polyquaternium-22, Polyquaternium-39, Polyquaternium-28, Polyquaternium-2, Polyquaternium-10, Polyquaternium-11, and also Polyquaternium 37&mineral oil&PPG trideceth (Salcare SC95), PVP-dimethylaminoethyl methacrylate copolymer, guar-hydroxypropyltriammonium chlorides, and also calcium alginate and ammonium alginate. Also suitable are cationic cellulose derivatives; cationic starch; copolymers of diallylammonium salts and acrylamides; quaternized vinylpyrrolidone/vinylimidazole polymers; condensation products of polyglycols and amines; quaternized collagen polypeptides; quaternized wheat polypeptides; polyethyleneimines; cationic silicone polymers, such as amidomethicones, for example; copolymers of adipic acid and dimethylaminohydroxypropyldiethylenetriamine; polyaminopolyamide and cationic chitin derivatives, such as chitosan, for example.

Examples of suitable silicone compounds are dimethylpolysiloxane, methylphenylpolysiloxanes, cyclic silicones, and amino-, fatty acid-, alcohol-, polyether-, epoxy-, fluoro- and/or alkyl-modified silicone compounds, and also polyalkylsiloxanes, polyalkylarylsiloxanes, polyethersiloxanes, as described in U.S. Pat. No. 5,104,645 and the documents cited therein, which at room temperature may be present either in liquid form or in resin form.

Suitable film formers, depending on the intended application, include salts of phenylbenzimidazolesulfonic acid, water-soluble polyurethanes, for example, $C_{10}$-polycarbamyl, polyglycerol esters, polyvinyl alcohol, polyvinylpyrrolidone, copolymers thereof, for example vinylpyrrolidone/vinyl acetate copolymer, water-soluble acrylic acid polymers/copolymers and their esters or salts, examples being partial ester copolymers of acrylic/methacrylic acid and polyethylene glycol ethers of fatty alcohols, such as acrylate/steareth-20 methacrylate copolymer, water-soluble cellulose, examples being hydroxymethylcellulose, hydroxyethylcellulose, hydroxypropylcellulose, water-soluble quaterniums, polyquaterniums, carboxyvinyl polymers, such as carbomers and their salts, polysaccharides, polydextrose for example, and glucan.

Examples of suitable antioxidants include superoxide dismutase, tocopherol (vitamin E), and ascorbic acid (vitamin C).

Suitable UV filters include 4-aminobenzoic acid; 3-(4'-trimethylammonium)benzylideneboran-2-one methylsulfate; 3,3,5-trimethylcyclohexyl salicylate; 2-hydroxy-4-methoxybenzophenone; 2-phenylbenzimidazole-5-sulfonic acid and its sodium, potassium, and triethanolamine salts; 3,3'-(1,4-phenylenedimethine)bis(7,7-dimethyl-2-oxobicyclo[2.2.1]heptane-1-methanesulfonic acid and its salts; 1-(4-tert-butylphenyl)-3-(4-methoxyphenyl)propane-1,3-dione, 3-(4'-sulfo)benzylidenebornan-2-one and its salts; 2-ethylhexyl 2-cyano-3,3-diphenylacrylate; polymer of N-[2(and 4)-(2-oxoborn-3-ylidenemethyl)benzyl]-acrylamide; 2-ethylhexyl 4-methoxycinnamate; ethoxylated ethyl 4-aminobenzoate; isoamyl 4-methoxycinnamate; 2,4,6-tris-[p-(2-ethylhexyloxycarbonyl)anilino]-1,3,5-triazine; 2-(2H-benzotriazol-2-yl)-4-methyl-6-(2-methyl-3-(1,3,3,3-tetramethyl-1-(trimethylsilyloxy)disiloxanyl)propyl)phenol; octyl methoxycinnamate; 4,4'-[(6-[4-((1,1-dimethylethyl)aminocarbonyl)phenylamino]-1,3,5-triazin-2,4-yl)-diimino]bis(benzoic acid 2-ethylhexyl ester); 3-(4'-methylbenzylidene)-D,L-camphor; 3-benzylidenecamphor; 2-ethylhexyl salicylate; 2-ethylhexyl 4-dimethylaminobenzoate; hydroxy-4-methoxybenzophenone-5-sulfonic acid (sulisobenzone) and sodium salt; and/or 4-isopropylbenzyl salicylate.

As superfatting agents it is possible to use substances such as, for example, polyethoxylated lanolin derivatives, lecithin derivatives, polyol fatty acid esters, monoglycerides, and fatty acid alkanol amides, the latter serving simultaneously as foam stabilizers.

Moisturizers available include for example isopropyl palmitate, glycerol and/or sorbitol.

Active biogenic substances are to be understood as including, for example, plant extracts and vitamin complexes.

Examples of suitable preservatives include phenoxyethanol, diazolidinylurea, parabens, pentanediol or sorbic acid.

Suitable preferred pearlizing components include fatty acid monoalkanol amides, fatty acid dialkanol amides, monoesters or diesters of alkylene glycols, especially ethylene glycol and/or propylene glycol or oligomers thereof, with higher fatty acids, such as palmitic acid, stearic acid, and behenic acid, monoesters or polyesters of glycerol with carboxylic acids, fatty acids and their metal salts, ketosulfones or mixtures of said compounds. Particular preference is given to ethylene glycol distearates and/or polyethylene glycol distearates having on average 3 glycol units.

As deodorizers it is possible, for example, to use allantoin and bisabolol in amounts by weight of from 0.0001% to 10%.

Suitable active antifungal substances (fungicides) include preferably ketoconazole, oxiconazole, bifonazole, butoconazole, cloconazole, clotrimazole, econazole, enilconazole, fenticonazole, isoconazole, miconazole, sulconazole, tioconazole, fluconazole, itraconazole, terconazole, naftifine and terbinafine, Zn pyrithione, and octopirox.

Particularly suitable thickeners and dispersants are ethylene glycol esters of fatty acids having 14 to 22, more preferably 16 to 22, carbon atoms, especially mono- and di-ethylene glycol stearate. Likewise of preferred suitability are stearic monoethanolamide, stearic diethanolamide, stearic isopropanolamide, stearic monoethanolamide stearate, stearyl stearate, cetyl palmitate, glyceryl stearate, stearamide diethanolamide distearate, stearamide monoethanolamide stearate, N,N-dihydrocarbyl-($C_{12}$-$C_{22}$)-amidobenzoic acid and its soluble salts, N,N-dihydrocarbyl-($C_{16}$-$C_{18}$)-amidobenzoic acid and its soluble salts, and N,N-di($C_{16}$-$C_{18}$)-amidobenzoic acid and derivatives thereof. Also of particular suitability are polyacrylates and carbomers, particularly those water-soluble or water-swellable copolymers based on acrylamidoalkylsulfonic acids and N-vinylcarboxamides.

Suitable solubilizers include in principle all monohydric or polyhydric alcohols and ethoxylated alcohols. Preferred alcohols are those having 1 to 4 carbon atoms, such as ethanol, propanol, isopropanol, n-butanol and iso-butanol, glycerol and mixtures thereof. Also of preference are polyethylene glycols having a relative molecular mass below 2000. Particular preference is given to polyethylene glycols having a relative molecular mass of between 200 and 600 in amounts of up to 45% by weight and polyethylene glycols having a relative molecular mass of between 400 and 600 in amounts from 0.5 to 15% by weight. Further suitable solvents are, for example, triacetin (glyceryl triacetate) and 1-methoxy-2-propanol.

As stabilizers it is possible to use metal salts of fatty acids, such as magnesium, aluminum and/or zinc stearate, for example.

The compositions of the invention can be blended with conventional ceramides, pseudoceramides, fatty acid N-alkylpolyhydroxyalkyl amides, cholesterol, cholesterol fatty acid esters, fatty acids, triglycerides, cerebrosides, phospholipids, and similar substances as a care additive.

The compositions normally possess a pH in the range from 2 to 12, preferably from 3 to 8.

The compositions of the invention can be any of a very wide variety of cosmetic and dermatological preparations. In particular they can be makeups, foundations, face powders, rouge, mascara, eyeshadows, eyeliners, lipsticks, creams, hair colorants, sunscreens, nail lacquers, and colored gels.

The examples and applications which follow are intended to illustrate the invention, though without restricting it thereto (all percentages are by weight). The copolymers used in the examples are representatives of the particularly preferred copolymers 1 to 67 already listed in the description. They were prepared by the therein-indicated processes 1, 2, 3 or 4 using the respectively preferred initiators and solvents.

EXAMPLE 1

Cosmetic Base

| Kaolin modified with SiO2 | 2.5% |
|---|---|
| Copolymer 66 | 0.4% |
| Glycereth-26 | 4.0% |
| Silica | 1.0% |
| Di-$C_{12}$-$C_{13}$-alkyl malates | 11.0% |
| Iron oxides | 1.25% |
| Titanium oxide | 5.0% |
| Neopentyl glycol diheptanoate | 3.0% |
| Diethylene glycol dioctanoate/diisononanoate | 3.5% |
| Tridecyl neopentanoate | 2.0% |
| Tocopherol acetate | 0.2% |
| Myristyl lactate | 2.0% |
| Cyclomethicone & dimethiconol | 1.0% |
| Porphyridium cruentum extract | 5.0% |
| Perfume oil | 0.4% |
| Preservative | 0.5% |
| Deionized water | ad 100 |

Preparation:

The oil phase is heated to 80° C., the pigments are added in glycereth-25 or PEG 8. The water, too, is heated to 80° C., AMPS copolymer is added, and the two phases are emulsified at 8000 rpm. The product was subsequently deaerated with slow stirring (about 200 rpm) and cooled.

EXAMPLE 2

Cosmetic Foundation with Sunscreen

| PEG-8 or glycereth-25 | 4.0 |
|---|---|
| Copolymer 41 | 0.4 |
| Iron oxides | 1.25 |
| Titanium oxide | 5.0 |
| Tocopherol acetate | 0.2 |
| C12-C13-Alkyl octanoate | 18.0 |
| Octyl methoxycinnamate | 7.0 |
| Preservative | 0.5 |
| Deionized water | ad 100 |

Preparation:

The oil phase is heated to 80° C., the pigments are added in glycereth-25 or PEG 8. The water, too, is heated to 80° C., polyquaternium is added, and the two phases are emulsified at 8000 rpm. The product was subsequently deaerated with slow stirring (about 200 rpm), at about 60° C. octyl methoxycinnamate was added, and the product was slowly cooled further.

EXAMPLE 3

Mascara

| Polyvinylpyrrolidone | 4.0 |
|---|---|
| Copolymer 67 | 0.2 |
| Glycereth-26 | 2.0 |
| Triethanolamine 99% | 2.4 |
| Magnesium aluminum silicate | 1.0 |
| Talc | 1.0 |
| Wheatgerm oil | 1.0 |
| PVP/eicosene copolymer | 2.0 |
| Iron oxides | 12.0 |
| Hydrogenated polyisobutene | 0.2 |
| Cetearyl alcohol | 0.1 |
| Stearic acid | 4.0 |
| Carnauba | 4.0 |
| Sorbitan sesquioleate | 1.3 |
| Beeswax | 4.0 |
| $C_{18}$-$C_{36}$ triglyceride | 8.5 |
| Lecithin | 1.0 |
| Tocopherol acetate | 0.2 |
| Preservative | 0.7 |
| Deionized water | ad 100 |

The gels and polymers were dispersed in the aqueous phase. Then the pigments were dispersed. The emulsion was finished at 85° C.

EXAMPLE 4

Makeup

| A | Cyclomethicone | 20.00 |
|---|---|---|
|   | Copolymer 32 with cyclomethicone | 9.00 |
| B | Titanium dioxide | 8.33 |
|   | Iron oxide, yellow | 1.35 |
|   | Iron oxide, red | 0.26 |

| | | |
|---|---|---|
| | Iron oxide, black | 0.06 |
| | Zinc oxide | 5.00 |
| C | Phenylbenzimidazolesulfonic acid | 5.20 |
| | Deionized water | 1.80 |
| | Triethanolamine | 3.00 |
| | Polysorbate-20 | 0.05 |
| | Deionized water | ad 100 |
| D | Methylparaben | 0.50 |
| E | Silica | 1.00 |

Preparation:

B was added with stirring at room temperature to A, then C, subsequently D and E were added to the homogeneous mixtures.

What is claimed is:

1. A method for decorating skin comprising contacting the skin with a cosmetic or dermatological composition comprising at least one copolymer obtained by free-radical copolymerization of
    A) acryloyldimethyltaurine and/or acryloyldimethyltaurates,
    B) optionally, one or more further olefinically unsaturated, noncationic, comonomers which have at least one oxygen, nitrogen, sulfur or phosphorus atom and possess a molecular weight of less than 500 g/mol,
    C) optionally, one or more olefinically unsaturated, cationic comonomers which have at least one oxygen, nitrogen, sulfur or phosphorus atom and possess a molecular weight of less than 500 g/mol,
    D) one or more at least monofunctional silicon-containing components capable of free-radical polymerization, at least one silicon-containing component being a compound selected from the group consisting of

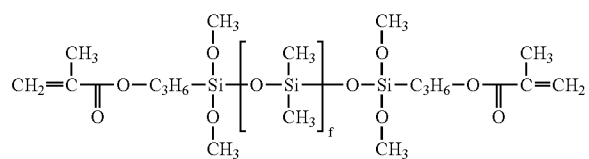

in which f=2 to 500,

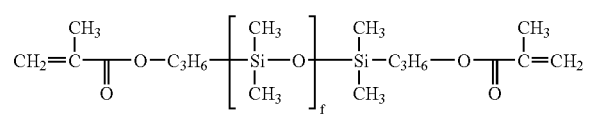

in which f=2 to 500,

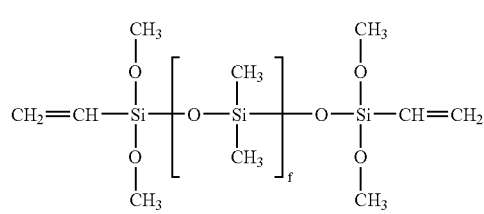

in which f=2-500, and mixtures thereof,

E) optionally, one or more fluorine-containing components capable of free-radical polymerization and having a functionality of at least one,
F) optionally, one or more olefinically mono- or polyunsaturated, macromonomers each possessing at least one oxygen, nitrogen, sulfur or phosphorus atom and having a number-average molecular weight of greater than or equal to 200 g/mol, the macromonomers not being a silicon-containing component D) or fluorine-containing component E),
G) optionally, the copolymerization taking place in the presence of at least one polymeric additive having a number-average molecular weight of from 200 g/mol to $10^9$ g/mol.

2. The method of claim 1, wherein said comonomers B) are selected from the group consisting of unsaturated carboxylic acids, salts of unsaturated carboxylic acids, anhydrides of unsaturated carboxylic acids, esters of unsaturated carboxylic acids with aliphatic, olefinic, cycloaliphatic, arylaliphatic or aromatic alcohols having 1 to 22 carbon atoms, open-chain N-vinyl amides, cyclic N-vinyl amides having a ring size of from 3 to 9, amides of acrylic acid, amides of methacrylic acid, amides of substituted acrylic acids, amides of substituted methacrylic acids, 2-vinylpyridine, 4-vinylpyridine, vinyl acetate, styrene, acrylonitrile, vinyl chloride, vinylidene chloride, tetrafluoroethylene, vinylphosphonic acid or the esters or salts thereof, vinylsulfonic acid or the esters or salts thereof, allylphosphonic acid or the esters or salts thereof, methallylsulfonic acid or the esters or salts thereof, and mixtures thereof.

3. The method of claim 1, wherein the comonomers C) are selected from the group consisting of diallyldimethylammonium chloride (DADMAC),
    [2-(methacryloyloxy)ethyl]trimethylammonium chloride (MAPTAC),
    [2-(acryloyloxy)ethyl]trimethylammonium chloride,
    [2-methacrylamidoethyl]trimethylammonium chloride,
    [2-(acrylamido)ethyl]trimethylammonium chloride,
    N-methyl-2-vinylpyridinium chloride,
    N-methyl-4-vinylpyridinium chloride,
    dimethylaminoethyl methacrylate,
    dimethylaminopropylmethacrylamide,
    methacryloylethyl N-oxide
    methacryloylethylbetaine, and mixtures thereof.

4. The method of claim 1, wherein the fluorine-containing components E) are compounds of the formula (II)

$$R^1—Y—C_rH_{2r}C_sF_{2s}CF_3 \quad (II)$$

where
    $R^1$ is a polymerizable function from a group of a vinylically unsaturated compound
    Y is a chemical bridge, and
    r, s are stoichiometric coefficients which independently of one another can be numbers between 0 and 200.

5. The method of claim 1, wherein said macromonomers F) are compounds of the formula (III)

$$R^1—Y—[(A)_v-(B)_w-(C)_x-(D)_z]-R^2 \quad (III)$$

where
    $R^1$ is a polymerizable function from a group of a vinylically unsaturated compound;
    Y is a bridging group;
    A, B, C, and D independently of one another are discrete chemical repeating units;
    v, w, x, and z independently of one another amount to from 0 to 500, the sum of v, w, x, and z being on average ≦1; and $R^2$ is a linear or branched aliphatic, olefinic, cycloaliphatic, arylaliphatic or aromatic ($C_1$-$C_{50}$) hydrocarbon radical, OH, —$NH_2$ or —$N(CH_3)_2$ or is [—Y—$R^1$].

6. The method of claim 1, wherein the polymeric additive G) is selected from the group consisting of polyalkylerte glycol, alkyipolyglycol, and mixtures thereof or a homopolymer or copolymer of a compound selected from the group consisting of N-vinylformamide, N-vinylacetamide, N-vinyipyrrolidone, ethylene oxide, propylene oxide, acryloyldimethyltaurine, N-vinylcaprolactam, N-vinylmethylacetamide, acrylamide, acrylic acid, methacrylic acid, N-vinylmorpholide, hydroxymethyl methacrylate, diallyldimethylammonium chloride (DADMAC), [2-(methacryloyloxy)ethyl] trimethylammonium chloride (MAPTAC), and mixtures thereof.

7. The method of claim 1, wherein the copolymerization takes place in the presence of at least one polymeric additive G).

8. The method of claim 1, wherein the copolymers are crosslinked.

9. The method of claim 1, wherein the copolymers are prepared by precipitation polymerization in tert-butanol.

10. The method of claim 1, wherein the copolymers are water-soluble or water-swellable.

11. The method of claim 1, wherein said compositions comprise, based on a finished composition, from 0.01 to 10% by weight of the copolymers.

12. The method of claim 1, wherein the compositions comprise pigments in the form of metal oxides, or wherein the compositions comprise pigments in the form of pigments modified with cationic coating shells.

13. The method of claim 1, wherein said cosmetic or dematological composition is selected from the group consisting of foundations, face powders, rouge, mascara, eyeshadows, eyeliners, lipsticks, creams, hair colorants, sunscreens, nail lacquers, and colored gels.

14. The method of claim 1, wherein the one or more further olefinically unsaturated, noncationic, comonomers B) are crosslinking.

15. The method of claim 1, wherein the one or more olefinically mono- or polyunsaturated, macromonomers F) are crosslinking.

16. The method of claim 4 wherein, $R^1$ is a radical selected from the group consisting of vinyl, allyl, methallyl, methylvinyl, acryloyl, methacryloyl, crotonyl, senecionyl, itaconyl, maleyi, fumaryl, styryl, and mixtures thereof.

17. The method of claim 4, wherein the chemical bridge Y is selected from the group consisting of —O—, —C(O)—, —C(O)—O—, —S—, —O—$CH_2$—CH(O—)—$CH_2$OH, —O—$CH_2$—CH(OH)—$CH_2$—O—, —O—$SO_2$—O—, —O—S(O)—O—, —PH—, —P($CH_3$)—, —$PO_3$—, —NH—, —N($CH_3$)—, —O—($C_1$—$C_{50}$)alkyl—O—, —O—phenyl—O—, —O—benzyl—O—, —O—($C_5$—$C_8$)cycloalkyl—O—, [$CH_2CH_2$—O]$_m)_o$—, where n, m, and o independently of one another denote numbers from 0 to 200.

18. The method of claim 5, wherein $R^1$ is a radical selected from the group consisting of vinyl, allyl, methallyl, methylvinyl, acryloyl, methacryloyl, crotonyl, senecionyl, itaconyl, maleyl, fumaryl, styryl, and mixtures thereof.

19. The method of claim 5, wherein the bridging group Y is selected from the group consisting of —O—, —S—, —C(O)—, —C(O)—O—, —O—$CH_2$—CH(O—)—$CH_2$OH, —O—$CH_2$—CH(OH)—$CH_2$O—, —C—$SO_2$—O—, —O—$SO_2$—O—, —O—SO—O—, —PH—, —P($CH_3$)—, —$PO_3$—, —NH—, —N($CH_3$)—, and mixtures thereof.

20. The method of claim 5 wherein the discrete repeating units of A, B, C, and D are originating from a unit selected from the group consisting of acrylamide, methacrylamide, ethylene oxide, propylene oxide, AMPS, acrylic acid, methacrylic acid, methyl methacrylate, acrylonitrile, maleic acid, vinyl acetate, styrene, 1,3-butadiene, isoprene, isobutene, diethylacrylamide, and diisopropylacrylamide.

21. The method of claim 5 wherein the discrete repeating units of A, B, C, and D are originating from a unit of ethylene oxide or propylene oxide.

22. The method of claim 5, wherein v, w, x, and z independently of one another amount to from 1 to 30.

23. The method of claim 12 wherein the metal oxides are selected from the group consisting of iron oxide, mica-iron oxide, titanium oxide, mica-titanium oxide, ultramarine blue, chromium oxide; and mixtures thereof.

24. The method of claim 12 wherein the cationic coating shells are selected from the group consisting of $SiO_2$, silica, ZnO, kaolin, $SiO_2$-modified kaolin, polytetrafluoroethylene, nylon, talc, mica, polymethyl methacrylate, polyethylene, and mixtures thereof.

25. A method for decorating skin comprising contacting the skin with a cosmetic or dermatological composition comprising at least one copolymer obtained by free-radical polymerization of the following components:
a) acryloyldimethyltaurine and/or an acryloyldimethyltaurate; and
b) one or more at least monofunctional silicon-containing component capable of free-radical polymerization, at least one silicon-containing component being a compound selected from the group consisting of

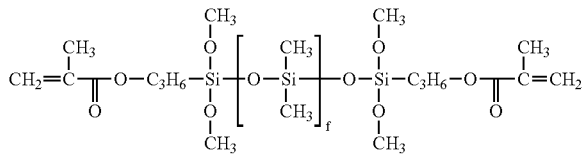

in which f=2 to 500,

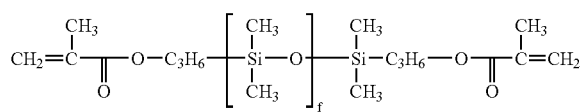

in which f=2 to500,

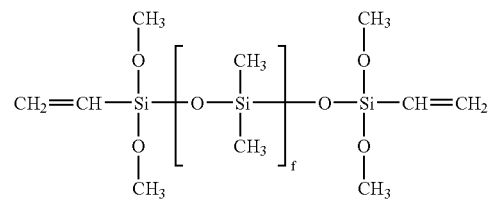

in which f=2-500, and mixtures thereof.

26. The method of claim 25, further comprising one or more component selected from the group consisting of the following components:
c) one or more further olefinically unsaturated, noncationic, comonomer having at least one oxygen, nitrogen sulfur or phosphorous atom and having a molecular. weight less than 500 g/mol;

d) one or more olefinically unsaturated, cationic comonomer having at least one oxygen, nitrogen sulfur or phosphorous atom and having a molecular weight less than 500 g/mol;

e) one or more fluorine-containing component capable of free-radical polymerization and having functionality of at least one; and d) one or more olefinically mono- or polyunsaturated, macromonomers each having at least one oxygen, nitrogen, sulfur, or phosphorous atom and having a number average molecular weight of greater than or equal to 200 g/mol, wherein said macromonomer is not said monofunctional silicon-containing component b) or said fluorine-containing component e).

27. The method of claim 25, wherein the copolymerization is carried out in the presence of at least one polymeric additive having a molecular weight of from 200 g/mol to $10^9$ g/mol.

28. The method of claim 26, wherein said macromonomer d) is crosslinking.

29. The method of claim 26, wherein said olefinically unsaturated, noncationic comonomer c) is crosslinking.

* * * * *